US006318362B1

(12) United States Patent
Johnson

(10) Patent No.: US 6,318,362 B1
(45) Date of Patent: *Nov. 20, 2001

(54) NASAL DILATOR

(75) Inventor: Bruce C. Johnson, St. Paul, MN (US)

(73) Assignee: Creative Integration & Design, Inc., St. Paul, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/874,781

(22) Filed: Jun. 13, 1997

Related U.S. Application Data

(63) Continuation of application No. 08/615,814, filed on Mar. 14, 1996, now abandoned, which is a continuation of application No. 08/183,916, filed on Jan. 19, 1994, now Pat. No. 5,533,499, which is a continuation of application No. 08/048,589, filed on Apr. 16, 1993, now abandoned, which is a continuation of application No. 07/884,626, filed on May 15, 1992, now abandoned, which is a continuation of application No. 07/712,508, filed on Jun. 10, 1991, now abandoned.

(51) Int. Cl.[7] ................................................ A61M 15/00

(52) U.S. Cl. ................................ 128/200.24; 128/207.18; 606/199; 606/204.45

(58) Field of Search ..................... 128/200.24, 204.12, 128/207.18, 848, 858, 912, DIG. 26; 606/191, 196, 198, 199, 204.45; 602/5, 6, 12, 14, 16, 17, 46, 47, 61, 74

(56) References Cited

U.S. PATENT DOCUMENTS

| | | |
|---|---|---|
| 850,978 | 4/1907 | Soares . |
| 1,043,924 | 11/1912 | Gottlieb . |
| 1,292,083 | 1/1919 | Sawyer . |
| 1,950,839 | 3/1934 | Chirila . |
| 2,001,862 | 5/1935 | Battey . |
| 2,398,073 | 4/1946 | Bonde . |
| 2,509,157 | 5/1950 | Lind . |
| 2,566,148 | 8/1951 | Sky . |

(List continued on next page.)

FOREIGN PATENT DOCUMENTS

| | | | |
|---|---|---|---|
| 453006 | 3/1926 | (DE) . | |
| 437661 | * 11/1926 | (DE) | ................................ 606/204.45 |
| 289561 | 10/1985 | (ES) | ................................ 128/200.24 |

OTHER PUBLICATIONS

Copy of Packaging containing a Nasal Strip sold prior to the filing of this application by Bolinger Industries.

Primary Examiner—Aaron J. Lewis
(74) Attorney, Agent, or Firm—Kinney & Lange

(57) ABSTRACT

A nasal dilator that prevents the outer wall tissue of the nasal passages of the nose from drawing in during breathing comprises a truss member. The truss member includes a flexible strip of material having a first end region, a second end region and an intermediate segment. The first and second end regions are adapted to engage the outer wall tissue of first and second nasal passages of the nose. The intermediate segment is configured to traverse a portion of a nose located between the first and second nasal passages. The truss member further includes first and second resilient bands secured to the strip of material adjacent opposite edges of the intermediate segment. The resiliency of the first and second resilient bands acts to stabilize the outer wall tissue and thereby prevents the outer wall tissue of the first and second nasal passages from drawing in during breathing.

34 Claims, 3 Drawing Sheets

U.S. PATENT DOCUMENTS

| | | |
|---|---|---|
| 2,586,219 | 2/1952 | Geffas . |
| 2,625,931 | 1/1953 | Phillips . |
| 3,046,989 | 7/1962 | Hill . |
| 3,426,751 | 2/1969 | Radewan . |
| 3,531,090 | 9/1970 | Laible . |
| 3,742,943 * | 7/1973 | Malmin ........................ 606/204.45 |
| 3,835,848 | 9/1974 | Berner . |
| 3,935,859 | 2/1976 | Doyle . |
| 4,153,051 | 5/1979 | Shippert . |
| 4,213,452 | 7/1980 | Shippert . |
| 4,274,402 | 6/1981 | Shippert . |
| 4,340,040 | 7/1982 | Straith . |
| 4,402,314 | 9/1983 | Goode . |
| 4,414,977 | 11/1983 | Rezakhany . |
| 4,534,342 | 8/1985 | Paxa . |
| 4,674,133 | 6/1987 | Oschner . |
| 4,823,789 * | 4/1989 | Beisang, III ................... 128/207.18 |
| 4,932,943 | 6/1990 | Nowak . |
| 4,971,282 | 11/1990 | Dickinson . |
| 4,984,302 | 1/1991 | Lincoln . |
| 4,995,114 | 2/1991 | Price, Jr. . |
| 5,003,971 | 4/1991 | Buckley . |
| 5,022,389 | 6/1991 | Brennan . |
| 5,101,837 | 4/1992 | Perrin . |
| 5,476,091 * | 12/1995 | Johnson ......................... 128/200.24 |
| 5,533,499 * | 7/1996 | Johnson ......................... 128/200.24 |
| 5,533,503 * | 7/1996 | Doubek et al. ................ 128/200.24 |
| 5,549,103 * | 8/1996 | Johnson ......................... 128/200.24 |

\* cited by examiner

NASAL DILATOR

This application is a continuation of application Ser. No. 08/615,814, filed Mar. 14,1996, now abandoned, which is a continuation of application Ser. No. 08/183,916, filed Jan. 19, 1994, now U.S. Pat. No. 5,533,499, which is a continuation of application Ser. No. 08/048,589, filed Apr. 16, 1993, now abandoned, which is a continuation of application Ser. No. 07/884,626, filed May 15, 1992, now abandoned, which is a continuation of application Ser. No. 07/712,508, filed Jun. 10, 1991, now abandoned.

BACKGROUND OF THE INVENTION

This invention relates generally to the field of devices for the treatment of malformations. In particular, the present invention is a nasal dilator for preventing outer wall tissue of nasal passages of a nose from drawing in during breathing.

A portion of the human population has some malformation of the nasal passages which makes breathing difficult. Example of such malformations are a deviated septum and swelling due to allergic reactions. The lower portion of the nostril, immediately above the entrance to the nostril, is known as a vestibule. The vestibule tapers inwardly to a narrowed neck-like area called the ostium internum. Above the ostium internum the nasal passages widen out again. Nasal obstructions commonly occur at the ostium in individuals who have swelling due to allergic reactions, a deviated septum or similar condition, to the point that the ostium may be substantially blocked. Commonly, the lateral wall (i.e., the outer wall tissue of the nasal passage) at the ostium is loose with the result that the outer wall tissue draws in during the process of inhalation to substantially block the passage of air through the nasal passage. The drawing in of the outer wall tissue act as a "check valve" to block air flow during in-breathing.

Blockage of the nasal passages is obviously an inconvenience to persons who experience it. In particular, sustained mouth breathing over a long period of time may cause lung irritation due to the inhalation of foreign particles that would otherwise be filtered if the breath had been passed through the nose. Blockage of the nasal passages is particularly uncomfortable at night, since it is uncomfortable for many people who have such a problem to breathe through the mouth while asleep. Nasal blockage can lead to sleep disturbances and irregularities, since a person with such a condition may wake often because he/she is not inhaling sufficient quantities of oxygen.

The most common approach to a serious and chronic nasal blockage problem as described above is a surgical attempt to correct the malformation of the nasal passages. However, surgery is expensive and may not ultimately correct the problem.

As an alternative to surgery, nasal dilators for aiding breathing through the nose are generally known. U.S. Pat. No. 4,414,977 to Rezakhany discloses one such nasal dilator. The nasal dilator includes generally elongated top and bottom rings which are spaced apart and connected together by a rear strut and a front strut. The front strut is longer than the rear strut and includes a bend therein formed at a position close to the front end of the bottom ring. When in place in the nasal passage, the top ring fits in the ostium within the nostril to prevent the tissue from being drawn in during inhalation, and to reduce extra flow resistance during exhalation. The bottom ring fits above the entrance to the nostril and serves to stabilize the position of the top ring within the nasal passage. One of these nasal dilators must be inserted into each nasal passage to provide unobstructed breathing.

However, these nasal dilators are not always effective since they are uncomfortable to wear. Because the nasal dilators must be inserted within the nasal passages they may cause irritation and itching. In addition, these nasal dilators must be custom-made to fit each nasal passage of an individual.

It is evident that there is a continuing need for improved nasal dilators for preventing outer wall tissue of nasal passages of a nose from drawing in during breathing. Specifically, there is a need for a nasal dilator that can provide effective relief without the need of inserting an object within the nasal passage. Moreover, there is a need for a nasal dilator that can be worn at night when the nasal blockage problem is most acute and most uncomfortable. The nasal dilator should be of efficient design and relatively uncomplicated and provide effective stabilization of the outer wall tissue of the nasal passages to provide effective relief from nasal blockage during inhalation. In addition, the nasal dilator should provide this effective stabilization without undue discomfort to the wearer.

SUMMARY OF THE INVENTION

The present invention is a nasal dilator for preventing outer wall tissue of nasal passages of a nose from drawing in during breathing. The nasal dilator comprises a truss member having a first end region adapted to engage the outer wall tissue of a first nasal passage. A second end region of the truss member is configured to engage the outer wall tissue of a second nasal passage. The first and second end regions of the truss member are coupled to one another by an intermediate segment. The intermediate segment is configured to traverse a portion of the nose located between the first and second nasal passages. The truss member, when in place, acts to stabilize the outer wall tissue and thereby prevent the outer wall tissue of the first and second nasal passages from drawing in during breathing.

The truss member includes a flexible strip of material that defines the first and second end regions and the intermediate segment of nasal dilator. A first resilient band is secured to a first side of the strip of material adjacent a first edge of the material. A second resilient band spaced from the first resilient band is secured to the first side of the strip of material adjacent a second edge thereof. The first and second resilient bands are oriented generally parallel to one another and substantially parallel to the longitudinal extent of the strip of material.

Each of the first and second resilient bands includes a plurality of grooves that extend substantially parallel to the respective resilient band. The grooves create areas of reduced material to enhance the flexibility of the first and second resilient bands in a direction perpendicular to the grooves. In addition, each of the first and second resilient bands includes first and second angled ends. The first and second angled ends extend towards the first side of the strip of material and help to prevent the first and second resilient bands from readily separating from the strip of material when the truss member is flexed. The resiliency of the first and second resilient bands prevent the outer wall tissue of the first and second nasal passages from drawing in during breathing.

The truss member further includes an adhesive substance located on a second side of the flexible strip of material. The adhesive substance acts to releasably secure the truss member to the outer wall tissue of the first and second nasal passages. First and second release liners cover the adhesive substance on the first and second end regions. The first and second release liners are readily removable from the strip of material to expose the adhesive substance and permit the truss member to be secured to the outer wall tissue of the first and second nasal passages.

This nasal dilator is of efficient design and effectively prevents the outer wall tissue of the first and second nasal passages of the nose from drawing in during breathing. In addition, the nasal dilator provides effective relief of nasal blockage during inhalation without the irritation and discomfort normally associated with nasal dilators that are inserted within the nasal passages. Moreover, this nasal dilator can be worn at night when the inhalation nasal blockage problem is most acute, without the anxiety and inconvenience normally associated with custom made, internally worn nasal dilators.

DETAILED DESCRIPTION OF THE PREFERRED EMBODIMENTS

Figure 1:
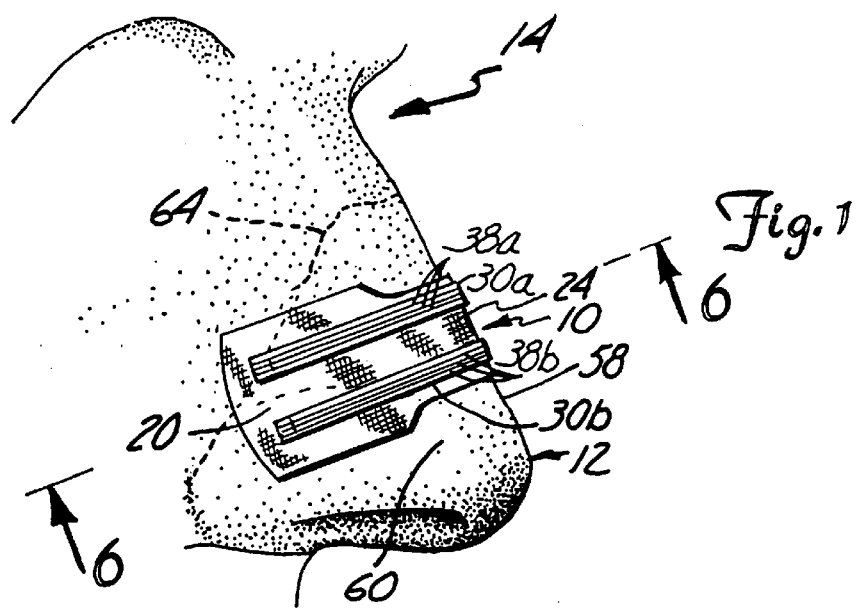
FIG. 1 is perspective view of a portion of a face with a nasal dilator in accordance with the present invention secured to a nose.

A nasal dilator 10 in accordance with the present invention is illustrated generally in FIG. 1. The nasal dilator 10 is shown secured to a nose 12 of a wearer 14.

Figure 2:
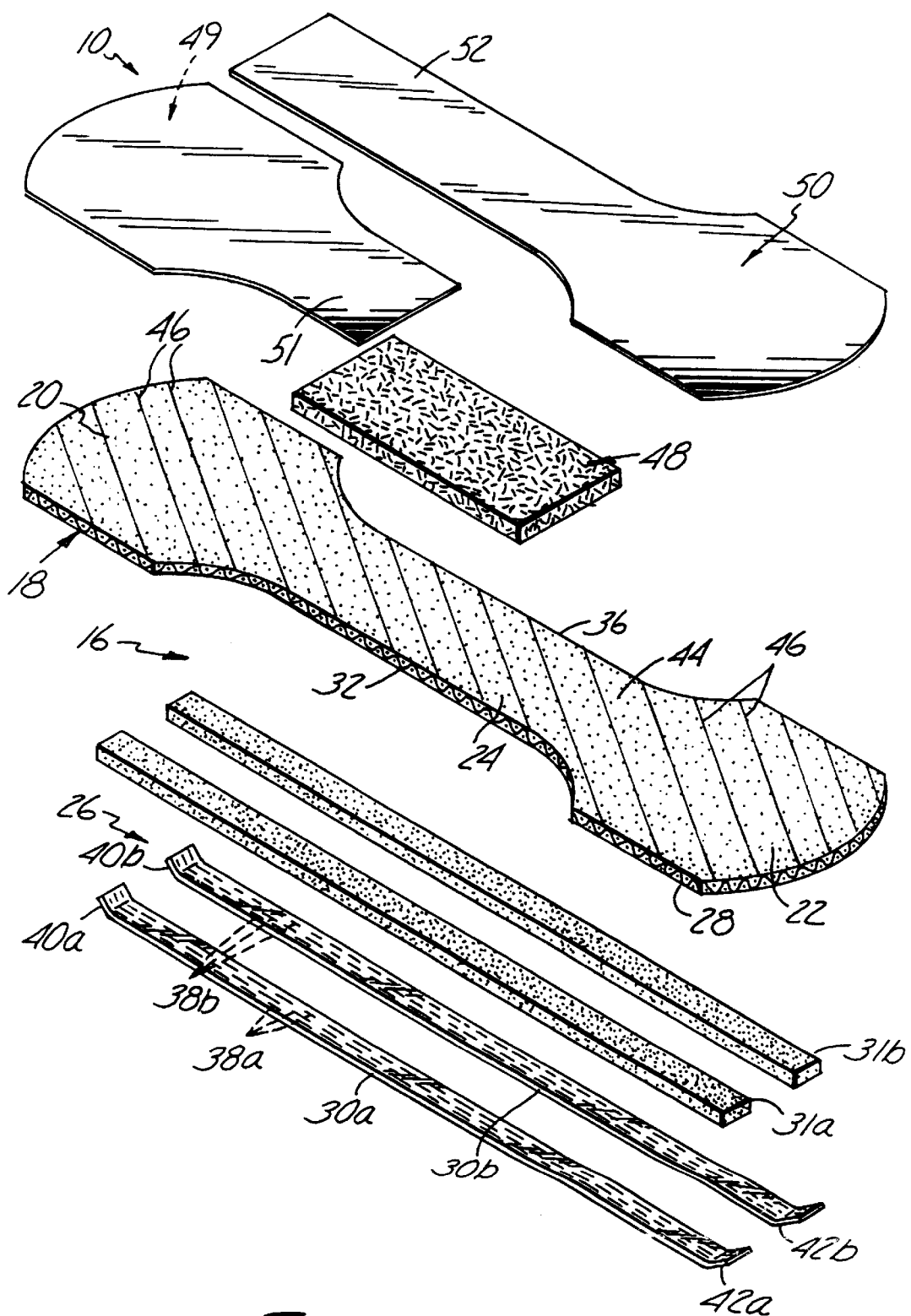
FIG. 2 is an exploded perspective view showing the components of the nasal dilator in accordance with the present invention.

As seen in FIG. 2, the nasal dilator 10 comprises a truss member 16 including a flexible strip of material 18 having a first end region 20 and a second end region 22 coupled to the first end region 20 by way of an intermediate segment 24. The width of the intermediate segment 24 is less than the width of the first and second end regions 20 and 22. The flexible strip of material 18 is preferably formed of an interwoven piece of fabric that allows the skin of the nose 12 to breathe to maximize comfort and minimize irritation. As an alternative, the strip of material 18 may be formed of a plastic film.

The truss member further includes resilient means 26 secured to a first side 28 of the strip of material 18. The resilient means 26 includes a first resilient band 30a secured by a first adhesive member 31 a to the first side 28 of the strip of material 18. The first resilient band 30a is secured to the strip of material 18 adjacent a first edge 32 of the intermediate segment 24. In addition, a second resilient band 30b, spaced from the first resilient band 30a, is secured by a second adhesive member 31b to the first side 28 of the strip of material 18. The second resilient band 30b is secured to the strip of material 18 adjacent a second edge 36 of the intermediate segment 24. The first and second resilient bands 30a and 30b are oriented generally parallel to one another and substantially parallel to the longitudinal extent of the flexible strip of material 18. Each of the first and second adhesive members 31 a and 31b is formed of an adhesive material such as double sided adhesive, foam tape.

Each of the first and second resilient bands 30a and 30b includes a plurality of grooves 38a and 38b, respectively, that extend substantially parallel to the respective resilient band 30a and 30b. As seen best in FIG. 2, the grooves 38a and 38b are formed in the exposed sides of the first and second resilient bands 30a and 30b (i.e., the sides of the first and second resilient bands 30a and 30b opposite that to which the first and second adhesive members 31a and 31b are secured). The grooves 38a and 38b create areas of reduced material to enhance the flexibility of the first and second resilient bands 30a and 30b in a direction perpendicular to the plurality of grooves 38a and 38b. In addition, each of the first and second resilient bands 30a and 30b includes first angled ends 40a and 40b, respectively, and second angled ends 42a and 42b, respectively. The first and second angled ends 40a,b and 42a,b extend towards the first side 28 of the strip of material 18 and help to prevent the first and second resilient bands 30a and 30b from readily separating from the strip of material 18 and the first and second adhesive members 31a and 31b when the truss member 10 is flexed. The first and second resilient bands 30a and 30b are formed of a plastic material.

As seen in FIG. 2, a second side 44 of the strip of material 18 includes a layer of an adhesive substance 46 that extends over the first and second end regions 20 and 22 and the intermediate segment 24. The adhesive substance 46 is bio-compatible with the skin of the nose 12. A padded element 48 is secured to the median of the intermediate segment 24 via the adhesive substance 46. Readily removable, first and second release liners 49 and 50, respectively, cover the adhesive substance 46 on the first and second end regions 20 and 22, respectively, of the strip of material 18. The first and second release liners 49 and 50 cover the adhesive substance 46 and remain in place on the strip of material 18 until the nasal dilator 10 is to be used. The first and second release liners 49 and 50 also include extensions 51 and 52, respectively, that cover the padded element 48 and further act to protect the padded element 48 until the nasal dilator 10 is to be secured to the nose 12 of a wearer 14.

Figure 3:
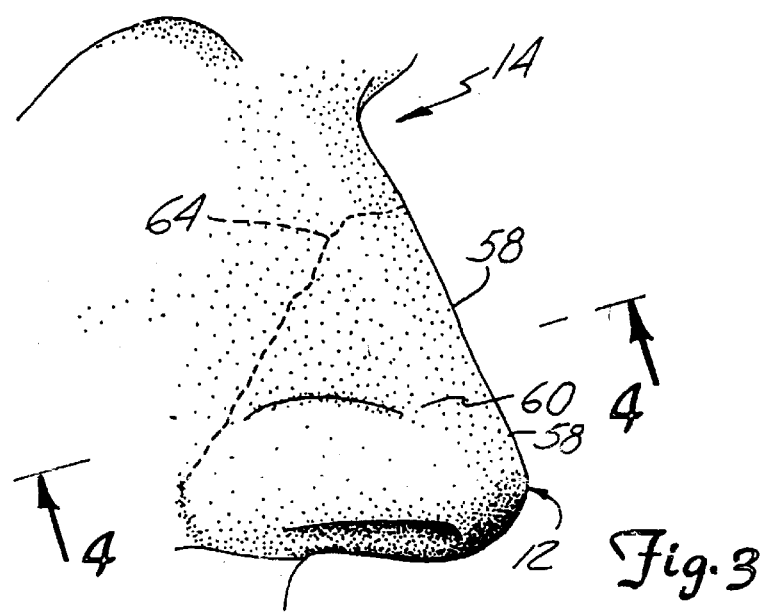
FIG. 3 is a perspective view similar to FIG. 1 with the nasal dilator in accordance with the present invention removed from the nose.
Figure 4:
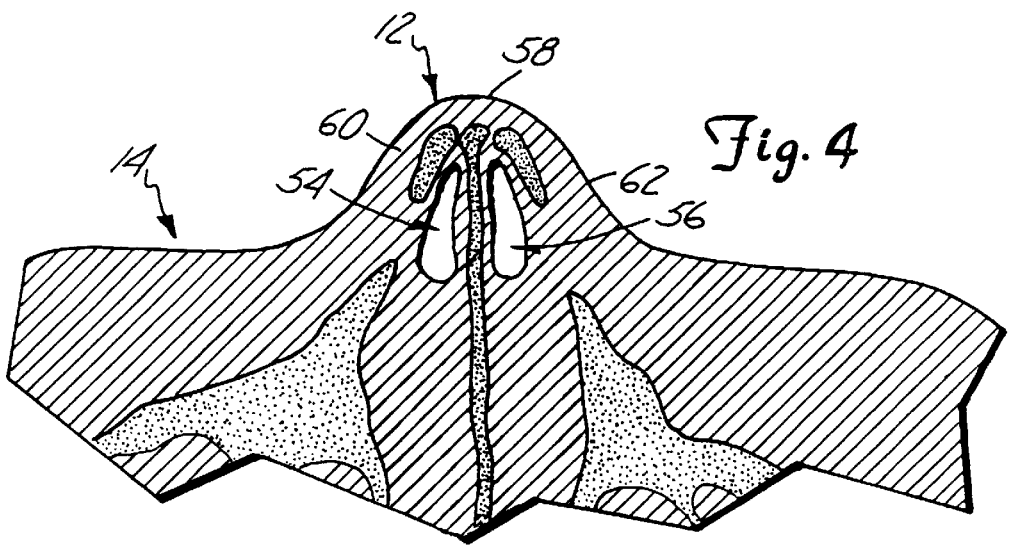
FIG. 4 is a sectional view taken along line 4—4 in FIG. 3 showing the nose in a state wherein no appreciable flow of air is occurring in the nasal passages.
Figure 5:
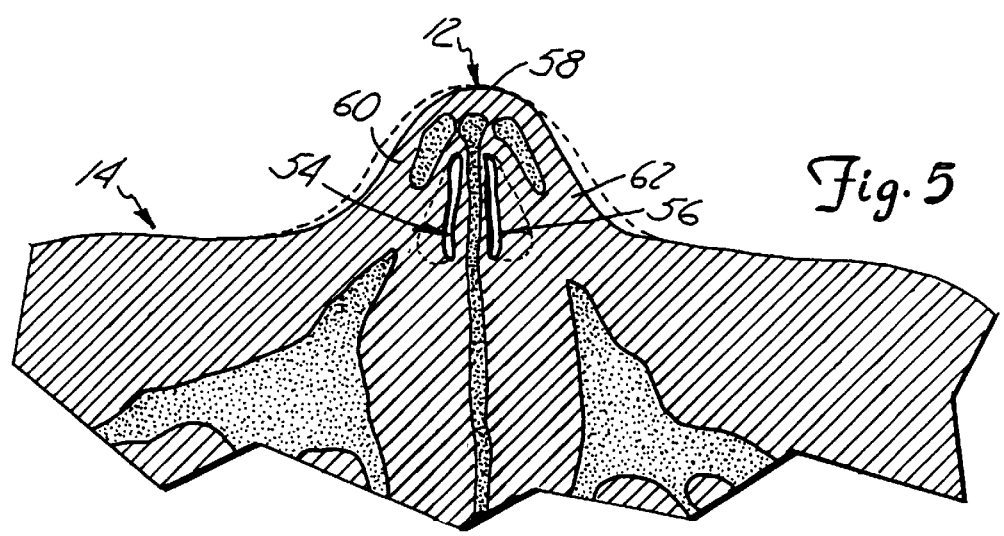
FIG. 5 is a sectional view similar to FIG. 4 showing the state of the nose during inhalation.

As seen in FIGS. 3 and 4, the nose 12 includes a first nasal passage 54, a second nasal passages 56 and a portion of the nose 12 known as the bridge 58 located between the first and second nasal passages 54 and 56. FIG. 4 shows the state of the first and second nasal passages 54 and 56 when no appreciable flow of air is occurring through the nasal passages 54 and 56. Due to a malformation, such as a deviated septum or swelling due to allergic reactions, outer wall tissue 60 and 62 of the first and second nasal passages 54 and 56, respectively, tends to be drawn in (i.e., collapse) during inhalation (see FIG. 5). This drawing in during inhalation is caused by reduced air pressure within the first and second nasal passages 54 and 56 as a result of an increase in air velocity as the in drawn breath travels through the first and second nasal passages 54 and 56. The portion (i.e., the ostium) of the outer wall tissue 60 and 62 drawn in during inhalation is that located between the nasal cartilage 64 (shown in dashed lines in FIGS. 1 and 3) and the entrance to the nasal passages 54 and 56. This drawing in of the outer wall tissue 60 and 62 causes nasal blockage. The nasal dilator 10 of the present invention remedies this problem.

Figure 6:
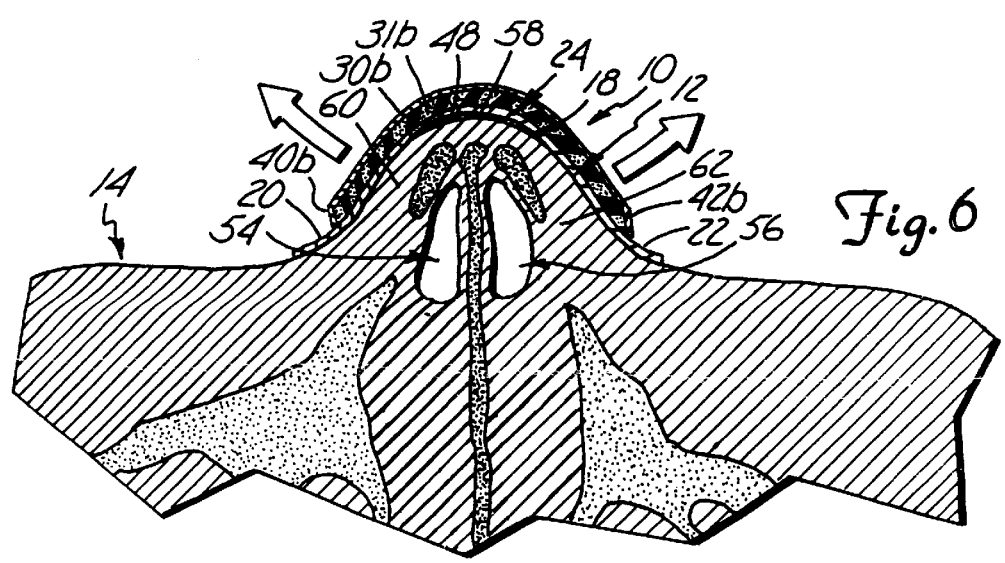
FIG. 6 is a sectional view taken along line 6—6 in FIG. 1 showing the state of the nose during inhalation with the nasal dilator in accordance with the present invention secured thereto.

To secure the nasal dilator 10 to the nose 12, the first and second release liners 49 and 50 are removed from the flexible strip of material 18 to expose the adhesive substance 46. As seen in FIGS. 1 and 6, the nasal dilator 10 is placed on the exterior of the nose 12 such that the intermediate segment 24 traverses the bridge 58 of the nose 12 and the first and second end regions 20 and 22 contact the outer wall tissue 60 and 62 of the first and second nasal passages 54 and 56. The adhesive substance 46 on the first and second end regions 20 and 22 releasably secures the truss member 16 to the outer wall tissue 60 and 62 of the first and second nasal passages 54 and 56. As seen in FIG. 6, the padded element 48 creates an absorbent adhesive void between the truss member 16 and the bridge 58. This absorbent adhesive void absorbs moisture due to perspiration or the like. With the nasal dilator 10 in place about the nose 12, the resiliency of the first and second resilient bands 30a and 30b (i.e., the tendency of the resilient bands to return to their normally planar state shown in FIG. 2) acts to stabilize the outer wall tissue 60 and 62 and thereby prevents the outer wall tissue 60 and 62 of the first and second nasal passages 54 and 56 from drawing in during breathing (i.e., during inhalation). In addition, the flexibility of the strip of material 18 and the first and second adhesive members 31a and 31b, the resiliency of the first and second bands 30a and 30b, and the flexibility of the first and second bands 30a and 30b due to the grooves 38a and 38b, all allow the nasal dilator 10 to closely conform to the curves of the nose of each individual wearer.

This nasal dilator 10 is of efficient design and effectively prevents the outer wall tissue 60 and 62 of the first and second nasal passages 54 and 56 of the nose 12 from drawing in during breathing. In addition, the nasal dilator 10 provides effective relief of nasal blockage during inhalation without the irritation and discomfort normally associated with nasal dilators that are inserted within the nasal passages. Moreover, this nasal dilator 10 can be worn at night when the inhalation nasal blockage problem is most acute, without the anxiety and inconvenience normally associated with custom made, internally worn nasal dilators.

Although the present invention has been described with reference to preferred embodiments, workers skilled in the art will recognize that changes may be made in form and detail without departing from the spirit and scope of the invention.

What is claimed is:

1. A nasal dilator for preventing outer wall tissue of nasal passages of a nose from drawing in during breathing comprising:
   a flexible truss member having an initial state absent fleaxure thereof the truss member including:
      a flexible strip of material defining first and second end regions and an intermediate segment with the first end region adapted to engage the outer wall tissue of a first nasal passage at a first side of the flexible strib of material and with the second end region adapted to engage the outer wall tissue of a second nasal passage at the first side of the flexible strip of material, the intermediate segment configured to traverse a portion of a user's name located between the first and second nasal passages, the tendency of the truss member to return to its initial state when flexed acting to stabilize the outer wall tissue and thereby prevent the outer wall tissue of the first and second nasal passages from drawing in during breathing; and
      a resilient member positioned adjacent a second side of the flexible strip of material so as together being capable, at least in part, of resilient deformation to allow the truss member to conform to the outer wall tissues of the first and second nasal passages and to provide said truss member with said tendency to return to its initial state when flexed.

2. The nasal dilator of claim 1, and further including:
   an adhesive substance located on the first side of the flexible strip of material at the first and second end regions thereof, so as together with the resilient member being capable, at least in part, of resilient deformation, the adhesive substance for releasably securing the truss member to the outer wall tissues of the first and second nasal passages.

3. The nasal dilator of claim 2, and further including:
   first and second release liners covering the adhesive substance on the first and second end regions, respectively, of the flexible strip of material, the first and second release liners being readily removable from the flexible strip of material to expose the adhesive substance and permit the truss member to be secured to the outer wall tissue of the first and second nasal passages.

4. The nasal dilator of claim 1 wherein the flexible strip of material is formed of a piece of fabric.

5. The nasal dilator of claim 1 wherein the resilient member includes:
   at least one resilient oriented substantially parallel to a longitudinal extent of the flexible strip of material, the resiliency of the at least one resilient band acting to prevent the outer wall tissue of the first and second nasal passages from drawing in during breathing.

6. The nasal dilator of claim 1 wherein said truss is of plastic construction.

7. A nasal dilator for preventing outer wall tissue of nasal passages of a user's nose from drawing in during breathing, comprising:
   a flexible truss member having an initial state absent flexure thereof, the truss member including:
      a first end region with an end region surface having an adhesive thereat so as to be adapted to adhesively engage the outer wall tissue of a first nasal passage;
      a second end region with an end region surface having an adhesive thereat so as to be adapted to adhesively engage the outer wall tissues of a second nasal passage;
      an intermediate segment configured to traverse a portion of the user's nose located between the first and second nasal passages; and
      a resilient member having an adhesive substance thereon, the resilient member having an adherence surface and being included in at least a portion of the first and second end regions and the intermediate segment, the resilient member having the adhesive substance thereon being on the adherence surface thereof which adherence surface faces at least in part the same way as do said first and second end region surfaces to thereby have said adhesives thereat available to engage the outer wall tissues, the resilient member being capable, at least in part, of resilient deformation that tends to cause the first and second end regions to separate from one another after being urged toward one another to give the truss member a tendency to return to its initial state when flexed to thereby act to stabilize the outer wall tissue if engaged therewith and so prevent the outer wall tissues of the first and second nasal passages from drawing in during breathing, the truss member including an adhesive void and configured to extend about a user's nose such that the intermediate segment traverses an exterior region of the bridge of a nose with the adhesive void located between the truss member and the bridge.

8. The nasal dilator of claim 7 wherein the resilient member includes:

at least one resilent band oriented substantially parallel to a longitudinal extent of the truss, the resiliency of at least one resilient band acting to prevent the outer wall tissue of the first and second nasal passages from drawing in during breathing.

9. The nasal dilator of claim 7 further including:

first and second release liners covering the first and second end regions, respectively, of the truss, the first and second release liners being readily removable from the truss first and second end regions to permit the truss member to be secured to the outer wall tissue of the first and second nasal passages.

10. The dilator of claim 7 wherein said void is provided by a separating material positioned between the remainder of the truss member and the exposed outer wall tissues of a user's nose.

11. The nasal dilator of claim 7 wherein said truss is of plastic construction.

12. A nasal dilator capable of introducing separating stresses in outer wall tissues of a user's nose, said dilator comprising:

a truss of plastic material comprising a flexible strip with a resilient member and a pair of spaced apart end surfaces such that forcing such end surfaces toward one another from initial positions to substantially reduce direct spacing therebetween by a spacing reduction force external to said truss results in restoring forces in said truss tending to restore said direct spacing between said end surfaces due to said resilient member; and engagement means adhered to said end surfaces and capable of engaging exposed surfaces of such outer wall tissues sufficiently to remain so engaged against said restoring forces, said flexible strip of material being positioned at least in part between any outer wall tissues engaged by said engagement means and said resilient member.

13. The nasal dilator of claim 12 wherein said truss is of plastic construction.

14. A nasal dilator capable of introducing separating stresses in outer tissues of a user's nose, said dilator comprising:

a truss having a pair of spaced apart end surfaces terminated by end edges at opposite ends of said truss, a resilient member, and a flexible strip of deformable material defining, at least in part, said pair of spaced apart end surfaces such that forcing said end surfaces toward one another from initial positions to substantially reduce direct spacing therebetween by a spacing reduction force external to said truss results in restoring forces in said truss tending to restore said direct spacing between said end surfaces due to said resilient member with said resilient member having opposite ends thereof each ending short of said end edges; and engagement means adhered to said end surfaces and capable of engaging exposed surfaces of such outer wall tissues sufficiently to remain so engaged against the said restoring forces, said resilient member being secured to a first side of said flexible strip of deformable material positioned between any outer wall tissues engaged by said engagement means and said resilient member.

15. The nasal dilator of claim 14 wherein said truss is of plastic construction.

16. A nasal dilator capable of introducing separating stresses in outer wall tissues of a user's nose, said dilator comprising:

truss having a plurality of resilient members therein and having a pair of spaced apart end surfaces such that forcing said end surfaces toward one another from initial positions to substantially reduce direct spacing therebetween by a spacing reducing force external to said truss results in restoring forces in said truss tending to restore said direct spacing between said end surfaces; and engagement means adhered to said end surfaces and capable of engaging exposed surfaces of such outer wall tissues sufficiently to remain so engaged against said restoring forces.

17. The dilator of claim 16 wherein said truss further comprises a flexible strip of deformable material with said plurality of resilient members being positioned adjacent a first side of said flexible strip of deformable material.

18. The nasal dilator of claim 16 wherein said truss is of plastic construction.

19. A nasal dilator capable of introducing separating stresses in outer wall tissues of an user's nose, said dilator comprising:

a truss having a resilient member therein and having a pair of spaced apart end surfaces with an intermediate segment therebetween such that forcing said end surfaces toward one another from initial positions to substantially reduce direct spacing therebetween by a spacing reduction force external to said truss results in restoring forces in said truss tending to restore said direct spacing between said end surfaces, said intermediate segment having an extent along a transverse direction substantially perpendicular to an extension direction extending along said intermediate segment and said end surfaces which is less than those extents of both said end surfaces along said transverse direction; and engagement means adhered to said end surfaces and capable of engaging exposed surfaces of such outer wall tissues sufficiently to remain so engaged against said restoring forces and to hold said truss substantially conformed about said outer wall tissues.

20. The dilator of claim 19 wherein said truss farther comprises a flexible strip of deformable material with said resilient member being positioned adjacent a first side of said flexible strip of deformable material.

21. The dilator of claim 19 wherein a plurality of resilient members are provided in said truss.

22. The dilator of claim 19 wherein a substantial portion of said intermediate segment is not so engaged with said outer wall tissues as are said end surfaces by said engagement means when concurrently in contact with those outer wall tissues.

23. The nasal dilator of claim 19 wherein said truss is of plastic construction.

24. A nasal dilator capable of introducing separating stresses in outer wall tissues of a user's nose, said dilator comprising:

a truss having a resilient member and adhesive therein and having a pair of spaced apart end surfaces with an intermediate segment therebetween such that forcing said end surfaces toward one another from initial positions to substantially reduce direct spacing therebetween by a spacing reduction force external to said truss results in restoring forces in said truss tending to restore said direct spacing between said end surfaces, said resilient member having an adherence surface with adhesive on that adherence surface thereof said adherence surface directions at least in part that are faced by said end surfaces of said truss; and engagement means adhered to said end surfaces and capable of sufficiently engaging exposed surfaces of such outer wall tissues adjacent thereto faced by said end surfaces to remain so engaged against said restoring forces and to hold said truss substantially conformed about said outer wall tissues but without at least a substantial portion of said intermediate segment being so engaged with said outer wall tissues adjacent thereto when concurrently in contact therewith.

25. The dilator of claim 24 wherein said truss further comprises a flexible strip of deformable material with said resilient member being positioned adjacent a first side of said flexible strip of deformable material.

26. The dilator of claim 24 wherein a plurality of separated resilient members are provided in said truss.

27. The dilator of claim 24 wherein that portion of said intermediate segment not so engaged with said outer wall tissues when concurrently in contact therewith is provided at least in part by a separating material positioned between the remainder of the truss member and the exposed outer wall tissues of a user's nose.

28. The nasal dilator of claim 24 wherein said truss is of plastic construction.

29. A nasal dilator capable of introducing separating stresses in outer wall tissues of a user's nose, said dilator comprising:

a truss having both a flexible strip of material and a resilient member adhered therein, and further having a pair of spaced apart end surfaces with an intermediate segment therebetween such that forcing said end surfaces toward one another from initial positions to substantially reduce direct spacing therebetween by a spacing reduction force external to said truss results in restoring forces in said truss tending to restore said direct spacing between said end surfaces, said resilient member having an adherence surface with an adhesive on that adherence surface thereof, said adherence surface facing directions at least in part that are faced by said end surfaces of said truss as adhered therein; and engagement means adhered to said end surfaces and capable of sufficiently engaging exposed surfaces of such outer wall tissues faced by said end surfaces to remain so engaged against said restoring forces.

30. The dilator of claim 29 wherein a plurality of resilient members are provided in said truss.

31. The dilator of claim 29 wherein a substantial portion of said intermediate segment is not so engaged with said outer wall tissues as are said end surfaces by said engagement means when concurrently in contact with those outer wall tissues.

32. The nasal dilator of claim 29 wherein said truss is of plastic construction.

33. A nasal dilator capable of introducing separating stresses in outer wall tissues of a user's nose, said dilator comprising:

a truss having both a flexible strip of material and a resilient member therein, and further having a pair of spaced apart end surfaces such that forcing said end surfaces toward one another from initial positions to substantially reduce direct spacing therebetween by a spacing reduction force external to said truss results in restoring forces in said truss tending to restore said direct spacing between said end surfaces, said resilient member and said flexible strip of material each having an adherence surface and with an adhesive on that adherence surface thereof, said adherence surfaces both facing directions at least in part that are faced by said end surfaces; and engagement means adhered to said end surfaces and capable of sufficiently engaging exposed surfaces of such outer wall tissues faced by said end surfaces to remain so engaged against said restoring forces including having any portions of said flexible strip of material positioned against these outer wall tissues as a result of such engaging thereof being directly adhered to those outer wall tissues.

34. The nasal dilator of claim 33 wherein said truss is of plastic construction.

* * * * *

UNITED STATES PATENT AND TRADEMARK OFFICE
CERTIFICATE OF CORRECTION

PATENT NO.     : 6,318,362 B1
DATED          : November 20, 2001
INVENTOR(S)    : Bruce C. Johnson It is certified that error appears in the above-identified patent and that said Letters Patent is hereby corrected as shown below:

Column 3,
Line 59, delete "31 a", insert -- 31a --

Column 4,
Line 5, delete "31 a", insert -- 31a --

Column 5,
Line 50, after "thereof", insert -- , --
Line 54, delete "strib", insert -- strip --
Line 59, delete "name", insert -- nose --

Column 6,
Line 27, after "resilient", insert -- band --

Column 8,
Line 6, before "truss", insert -- a --
Line 46, delete "farther", insert -- further --

Signed and Sealed this

Fourth Day of June, 2002

Attest:

JAMES E. ROGAN
Attesting Officer   Director of the United States Patent and Trademark Office

(12) EX PARTE REEXAMINATION CERTIFICATE (5471st)
United States Patent
Johnson

(10) Number: US 6,318,362 C1
(45) Certificate Issued: *Aug. 8, 2006

(54) NASAL DILATOR

(75) Inventor: Bruce C. Johnson, St. Paul, MN (US)

(73) Assignee: Creative Integration & Design, Inc., St. Paul, MN (US)

Reexamination Request:
No. 90/007,185, Aug. 23, 2004

Reexamination Certificate for:
Patent No.: 6,318,362
Issued: Nov. 20, 2001
Appl. No.: 08/874,781
Filed: Jun. 13, 1997

(*) Notice: This patent is subject to a terminal disclaimer.

Certificate of Correction issued Jun. 4, 2002.

Related U.S. Application Data

(63) Continuation of application No. 08/615,814, filed on Mar. 14, 1996, now abandoned, which is a continuation of application No. 08/183,916, filed on Jan. 19, 1994, now Pat. No. 5,533,499, which is a continuation of application No. 08/048,589, filed on Apr. 16, 1993, now abandoned, which is a continuation of application No. 07/884,626, filed on May 15, 1992, now abandoned, which is a continuation of application No. 07/712,508, filed on Jun. 10, 1991, now abandoned.

(51) Int. Cl.
*A61M 15/00* (2006.01)

(52) U.S. Cl. .............. 128/200.24; 128/207.18; 606/199; 606/204.45

(58) Field of Classification Search ............ None
See application file for complete search history.

(56) References Cited

U.S. PATENT DOCUMENTS 2,633,128 A * 3/1953 Schaefer ............... 602/42
RE35,408 E * 12/1996 Petruson ................ 128/858

FOREIGN PATENT DOCUMENTS

ES           289561        *  4/1986

* cited by examiner

*Primary Examiner*—Kenneth Bomberg

(57) ABSTRACT

A nasal dilator that prevents the outer wall tissue of the nasal passages of the nose from drawing in during breathing comprises a truss member. The truss member includes a flexible strip of material having a first end region, a second end region and an intermediate segment. The first and second end regions are adapted to engage the outer wall tissue of first and second nasal passages of the nose. The intermediate segment is configured to traverse a portion of a nose located between the first and second nasal passages. The truss member further includes first and second resilient bands secured to the strip of material adjacent opposite edges of the intermediate segment. The resiliency of the first and second resilient bands acts to stabilize the outer wall tissue and thereby prevents the outer wall tissue of the first and second nasal passages from drawing in during breathing.

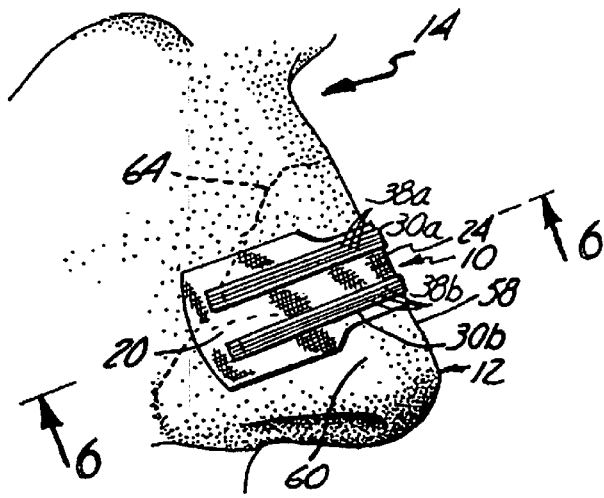

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–34 is confirmed.

* * * * *